US011534106B2

(12) United States Patent
Knuebel et al.

(10) Patent No.: US 11,534,106 B2
(45) Date of Patent: Dec. 27, 2022

(54) METHOD FOR DETERMINING A USER-SPECIFIC HAIR TREATMENT

(71) Applicant: Henkel AG & Co. KGaA, Duesseldorf (DE)

(72) Inventors: Georg Knuebel, Duesseldorf (DE); Antje Gebert-Schwarzwaelder, Neuss (DE); Astrid Kroos, Monheim (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 1007 days.

(21) Appl. No.: 16/311,849

(22) PCT Filed: Jul. 4, 2017

(86) PCT No.: PCT/EP2017/066580
§ 371 (c)(1),
(2) Date: Dec. 20, 2018

(87) PCT Pub. No.: WO2018/007358
PCT Pub. Date: Jan. 11, 2018

(65) Prior Publication Data
US 2019/0216387 A1   Jul. 18, 2019

(30) Foreign Application Priority Data

Jul. 5, 2016  (DE) .................... 10 2016 212 202.9
Nov. 11, 2016 (DE) .................... 10 2016 222 193.0

(51) Int. Cl.
| | |
|---|---|
| A61B 5/00 | (2006.01) |
| A61B 5/103 | (2006.01) |
| G01N 21/359 | (2014.01) |
| A61B 5/1455 | (2006.01) |
| A61B 5/145 | (2006.01) |
| G16H 20/00 | (2018.01) |
| A45D 44/00 | (2006.01) |

(52) U.S. Cl.
CPC ............. *A61B 5/448* (2013.01); *A45D 44/00* (2013.01); *A61B 5/0075* (2013.01); *A61B 5/1032* (2013.01); *A61B 5/1455* (2013.01); *A61B 5/14546* (2013.01); *A61B 5/44* (2013.01); *A61B 5/486* (2013.01); *A61B 5/7246* (2013.01); *G01N 21/359* (2013.01); *G16H 20/00* (2018.01); *A45D 2044/007* (2013.01); *A61B 2503/12* (2013.01); *A61B 2560/0223* (2013.01)

(58) Field of Classification Search
CPC ... A61B 5/448; A61B 5/1032; A61B 5/14546; A61B 5/1455; A61B 5/486; A61B 2560/0223; A45D 44/00; A45D 2044/007; G16H 20/00
See application file for complete search history.

(56) References Cited

U.S. PATENT DOCUMENTS

| | | | |
|---|---|---|---|
| 2002/0010556 A1 | 1/2002 | Marapane | |
| 2003/0051297 A1* | 3/2003 | Patel | A61K 8/02 |
| | | | 8/408 |
| 2006/0281994 A1 | 12/2006 | Miyamae | |
| 2008/0261315 A1* | 10/2008 | Strongin | G01N 33/6815 |
| | | | 436/106 |
| 2014/0118521 A1 | 5/2014 | Conti | |

FOREIGN PATENT DOCUMENTS

| | | |
|---|---|---|
| CN | 1440503 A | 9/2003 |
| DE | 102016212202 A1 | 1/2018 |
| JP | 2003270138 A | 9/2003 |
| JP | 2003344279 A | 12/2003 |
| JP | 2010112788 A | 5/2010 |
| WO | 2010076104 A2 | 7/2010 |
| WO | 2015166403 A1 | 11/2015 |

OTHER PUBLICATIONS

Watanabe et al. ("Cysteic Acid Formation Behaviors in Bleached Hair of Southeast Asian Characterized by Infrared Spectroscopy") (Year: 2015).*
Tate et al. ("Quantification and prevention of hair damage") (Year: 1993).*
Miyamae et al.: "Evaluation of Physical Properties of Human Hair by Diffuse Reflectance Near-Infrared Spectroscopy", Applied Spectroscopy, vol. 61, 2007, No. 2, pp. 212-217, Japan.
Rashaid et al.: "Amino acid composition of human scalp hair as a biometric classifier and investigative lead", Analytical Methods, vol. 7, 2015, pp. 1707-1718.
EPO, International Search Report issued in International Application No. PCT/EP2017/066580, dated Oct. 5, 2017.
Koji Takada et al: "Influence of Oxidative and/or Reductive Treatment on Human Hair (I): Analysis of Hair-Damage after Oxidative and/or Reductive Treatment", Journal of Oleo Science, vol. 52, No. 10, Jan. 1, 2003 (Jan. 1, 2003), pp. 541-548, XP055002836, ISSN: 1345-8957.

* cited by examiner

*Primary Examiner* — Christian Jang
(74) *Attorney, Agent, or Firm* — Lorenz & Kopf, LLP

(57) ABSTRACT

The present disclosure relates to a method for determining a user-specific hair treatment with determination and inclusion of the degree of damage of the hair. To this end, the content of cysteic acid is firstly determined with the aid of near-infrared and/or infrared spectra of the keratin fibres of an individual and a degree of damage is derived via a calibration model. Individual treatment advice is output on the basis of the determined degree of damage.

18 Claims, No Drawings

METHOD FOR DETERMINING A USER-SPECIFIC HAIR TREATMENT

CROSS-REFERENCE TO RELATED APPLICATION

This application is a U.S. National-Stage entry under 35 U.S.C. § 371 based on International Application No. PCT/EP2017/066580, filed Jul. 4, 2017 which was published under PCT Article 21(2) and which claims priority to German Application No. 10 2016 212 202.9, filed Jul. 5, 2016 and to German Application No. 10 2016 222 193.0, filed Nov. 11, 2016, which are all hereby incorporated in their entirety by reference.

TECHNICAL FIELD

The present disclosure relates to a method for determining a user-specific hair treatment.

BACKGROUND

An effect of the product in the treatment of hair with cosmetic products, for example an intensity of a colouring, can be heavily dependent on the degree of damage of the hair. In addition, damaged hair is often more difficult to handle and lacklustre.

There are many different haircare products on the market that are intended to improve different hair properties or parameters, such as shine. In many cases, however, the user of such products does not know how strong their hair is or in what way is damaged. This can mean that the user resorts to products that are less suitable for their specific case and is dissatisfied with the efficacy of these products after using them.

A determination of the damage of the hair may therefore be of great importance.

Hair can be damaged by natural or artificially induced processes. The most notable type of damage here can be oxidative damage.

The natural processes for example can include a combined (for example simultaneous) effect of UV light and oxygen ($O_2$) on the hair.

The artificially induced processes for example can include a use of hair dyes (also referred to as colorants), bleaching and/or the generation of permanent waves.

Besides the desired cosmetic effects, for example a lightening of the hair, the hair can also be heavily damaged, for example if oxidizing agents are used.

The damage process can be brought about by an oxidation of amino acids, for example an oxidation of the amino acids cystine and cysteine, which occur very often in the hair, into cysteic acid. Cystine can form intermolecular disulphide bridges (also referred to as S bridges) in the hair, such that cystine is extremely important for the mechanical stability of the hair.

The oxidation of these bridges to form cysteic acid can destroy the mechanical stability of the hair and can even lead to complete hair breakage in the case of repeated use. However, properties of the hair that previously could be perceived, for example felt, macroscopically, for example a surface roughness, can also be negatively influenced. Results of cosmetic treatments, in particular of damaging procedures, can be massively changed already in an early stage of damage compared to a result achieved with undamaged hair.

The described mechanism of damage makes it possible to precisely determine the degree of the most notable damage, specifically the oxidative damage, by determining the content of cysteic acid.

In an academic and industrial field, a large number of physical and chemical analytical methods may be available to a researcher or developer in order to determine a degree of damage, for example in order to quantitatively determine a degree of oxidative damage.

Usually, chromatographic methods are used here, such as high-performance liquid chromatography (HPLC) after a complex acidic hydrolytic decomposition of the hair sample.

Undamaged hair may typically have a cysteic acid content in the range of from approximately 0.5% to approximately 1% (based on weight). If there is damage, for example as a result of repeated ultra-bleaching and/or other mechanisms of damage, the cysteic content may be increased to more than about 15% (by weight).

However, all of these chromatographic methods are complicated and require a costly equipment set-up, such that they are not available to an end consumer.

Users of products increasingly desire a product adapted to their individual requirements. This is also true in particular for beauty products such as skin and/or hair treatment agents.

BRIEF SUMMARY

A method for determining an individualized hair treatment is provided herein. The method includes the step of determining the cysteic acid content of a number of samples of differently damaged keratin fibers by a chromatographic process. The method further includes recording near-infrared and/or infrared spectra of the samples of differently damaged keratin fibers. The method further includes creating a calibration model which produces a correlation between near-infrared and/or infrared spectra and the cysteic acid content. The method further includes recording near-infrared and/or infrared spectra of the keratin fibers of an individual. The method further includes determining the degree of damage of the keratin fibres of this individual on the basis of the calibration model. The method further includes outputting individual treatment advice regarding the keratin fibers of the individual depending on the determined degree of damage.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure was therefore to provide a method for determining individual hair treatment advice that allows an end user to determine the degree of damage, in particular in the form of a cysteic acid content, of their hair in a simple manner and to obtain hair treatment advice adapted thereto.

This object is achieved by a method for determining an individualized hair treatment comprising the following steps:

a) determining the cysteic acid content of a number of samples of differently damaged keratin fibres by employing a chromatographic process;

b) recording near-infrared and/or infrared spectra of the samples of differently damaged keratin fibres;
c) creating a calibration model which produces a correlation between near-infrared and/or infrared spectra and the cysteic acid content;
d) recording near-infrared and/or infrared spectra of the keratin fibres of an individual;
e) determining the degree of damage of the keratin fibres of this individual on the basis of the calibration model; and
f) outputting individual treatment advice regarding the keratin fibres of the individual depending on the determined degree of damage.

The terms "keratin fibre" and "human hair" within the scope of this application comprise furs, wool and feathers, but in particular human hair. The terms "hair" and "keratin fibre" are used synonymously.

Within the scope of this application a "user" or "consumer" may be the individual whose keratin fibers are being examined and for whom an individualised hair treatment is determined. Alternatively, a "user" or "consumer" may be a third party who examines the keratin fibers of an individual and for whom an individualized hair treatment is determined.

The near-infrared and/or infrared spectroscopy allows the direct, destruction-free determination of a degree of damage, in particular a cysteic acid content, without complex sample preparation and without changing or destroying the hair by analysis of the structure thereof. This has the advantage that the result can be very quickly obtained and the hair can be subjected to a treatment once the cysteic acid content has been determined. A further advantage is that the near-infrared and/or infrared spectroscopy can be performed on keratin fibres located on the head of the individual.

The claimed method firstly requires the creation of a calibration model. To this end, in a step a), the cysteic acid content of a number of samples of differently damaged keratin fibers is firstly determined by employing a chromatographic process, for example by employing HPLC.

In a step b) near-infrared and/or infrared spectra of the samples of differently damaged keratin fibers are then recorded.

The near-infrared (NIR) and/or an infrared (IR) spectra can be obtained, for example, by employing ATR (attenuated total reflection) (near-)infrared spectroscopy.

In step c) a calibration model is created which produces a correlation between the near-infrared and/or infrared spectra of the samples (calibration spectra) and the cysteic acid content of the samples that was determined by employing an independent chromatographic, colorimetric or electromagnetic process. The creation of the calibration model can also comprise the recording, for the plurality of calibration hair samples, of a calibration spectrum of at least part of the near-infrared and/or infrared light that is reflected and/or scattered by the calibration hair sample during exposure of the calibration hair sample to near-infrared and/or infrared light, determining of the degree of damage of the calibration hair sample by employing an independent chromatographic process, allocating of a degree of damage to the calibration spectrum, and determining of a correlation between the plurality of calibration spectra and the plurality of degrees of damage.

Steps a) and b) do not necessarily have to be carried out successively or in that order. Thus, step b) can be carried out first, followed then by step a).

In a preferred embodiment the calibration model from steps a) to c) is present in the form of stored information on a local data carrier or in a cloud. A local data carrier in the sense of this application comprises all physical carrier substances on which data can be recorded. In a particularly preferred embodiment the data carrier is identical to the data processing device to which the (N)IR spectrometers for recording near-infrared and/or infrared spectra of the keratin fibers are connected. This can be in particular a smart phone, a tablet, a laptop, a smart mirror or a computer. In an alternative embodiment the calibration model from steps a) to c) is present in the form of stored information in a cloud.

By use of mathematical models, a mathematical model can be created by measurement of calibration hair samples which have a cysteic acid content determined on the basis of a known analytical method which then allows a calculation/determination of a content of cysteic acid and thus of hair damage in a hair sample, also referred to as a braid, from the consumer on the basis of the recorded NIR and/or IR spectrum. An analysis of the spectrum and use of the model can be performed here for example (with suitable apps) by employing known data processing devices, such as smart phones, tablets, or the like by a cloud.

The mathematical model may be an artificial system that for example learns from the calibration hair samples and can generalize these once the learning phase is complete. This means that the examples are not simply memorized, but patterns and laws are identified in the learning data. Different approaches can be followed to this end. For example, a monitored learning, a partially monitored learning, an unmonitored learning, a corroborated learning and/or active learning can be used, in particular in conjunction with deep learning methods. Monitored learning can be implemented for example by employing an artificial neuronal network (for example a recurrent neuronal network) or by employing a support vector machine. Unmonitored learning can also be implemented for example by employing an artificial neuronal network (for example an auto encoder).

One possible calibration model is a multivariate calibration process, in which all absorption values measured at different wavelengths/wave numbers are included in the evaluation.

Further factors, in particular categorical factors, such as ethnicity of the individual, age of the individual (as category or metrically), hair color of the individual (as category or metrically) can also be taken into consideration in order to optimize the calibration model.

In the further course of the method, in step d) a near-infrared and/or infrared spectrum of the keratin fibres of an individual is recorded. This can be achieved for example in such a way that, during the exposure of a hair sample of the hair of the individual to near-infrared and/or infrared light, a spectrum of at least part of the near-infrared and/or infrared light that is reflected and/or scattered by the hair sample is recorded. A plurality of near-infrared and/or infrared spectra per measurement point are thus preferably recorded in step d) and averaged in each case.

In step e) the degree of damage of the keratin fibers of the individual is determined on the basis of the calibration model created in steps a) to c).

To this end, at least part of the near-infrared and/or infrared spectrum of the hair of the individual is compared with the calibration model for example, and a degree of damage of the hair is determined/allocated.

In a further advantageous embodiment the near-infrared and/or infrared spectra of the keratin fibres of an individual are/is recorded at different positions along the keratin fibres. The near-infrared and/or infrared spectra can thus be recorded at the start of and/or in the middle and/or at the tips of the keratin fibres. Accordingly, the degree of damage can be determined for each of these individual positions.

Near-infrared spectroscopy, similarly to other vibrational spectroscopies, is based on the excitation of molecule vibrations by electromagnetic radiation in the (near) infrared range. In near-infrared spectroscopy the detection takes place in the near infrared (from about 760 to about 2,500 nm or approximately 13,000-4,000 $cm^{-1}$) Hereinafter, the term near-infrared (NIR) shall be used for light with a wave number in a range of from about 12,820 to about 4,000 $cm^{-1}$ and the term infrared (IR) shall be used for light with a wave number in a range of from about 3,999 to about 400 $cm^{-1}$.

By use of miniaturised (N)IR spectrometers and the connection thereof to a mobile data processing device, the method and in particular step d) of the method can be performed for example in the private field by the individual themself, by any person at a point of sale (POS) of hair treatment agents, or by a hairdresser. In a preferred embodiment the mobile data processing device is a smart terminal, for example a smart phone, a tablet or a laptop.

The (N)IR spectrometers or (N)IR sensors can also be provided in particular in mobile form, for example in the form of hand-held spectrometers or attachment spectrometers.

An example of a suitable hand-held spectrometer is the "MicroNIR OnSite" from the company Viavi Solutions Inc. This spectrometer is supplied with power and controlled by a tablet or a laptop via a USB connection and makes it possible to record the near-infrared and/or infrared spectra of the keratin fibres of an individual in real time with a measurement time of between about 0.25 and about 0.5 seconds. The spectrometer comprises two integrated vacuum tungsten lamps and an InGaAs photodiode array with 128 pixels. The "MicroNIR OnSite" operates in a wave number range of from about 6,060 to about 10,526 $cm^{-1}$. The distance between the keratin fibres and the glass of the hand-held spectrometer can be between 0 and about 15 mm, wherein a distance of 3 mm is preferred.

In one embodiment as contemplated herein the entire method for determining an individualized hair treatment is performed by the tablet or the laptop which supplies power to and controls the "MicroNIR OnSite" spectrometer. Alternatively, the obtained spectroscopic data can be sent to a further (mobile) data processing device, in particular a further smart terminal, which them performs the method for determining an individualized hair treatment. The spectroscopic data can be transmitted for example wirelessly by employing WLAN (Wi-Fi) or Bluetooth.

A further suitable hand-held spectrometer is the "i-Spec Nano" by the company B&W Tek. The spectrometer is supplied with power via a USB connection and a (mobile) data processing device connected thereto or via a battery. The spectrometer comprises a light source and operates in a wave number range of from about 4,545 to about 7,692 $cm^{-1}$. The spectroscopic data is transmitted to a (mobile) data processing device, which then performs the method for determining an individualized hair treatment, wirelessly by employing WLAN (WiFi) or Bluetooth.

The "QualitySpec Trek" hand-held spectrometer from the company ASD Inc. is also suitable. It operates in a wave number range of from about 28,571 to about 400 $cm^{-1}$.

A further suitable hand-held spectrometer is the "SCiO by Consumer Physics", which displays the spectroscopic data on a smart terminal with the aid of the integrated app "SpectroScan". The hand-held spectrometer operates in the short-wave range of NIR, more specifically at wave numbers of from about 9,090 to about 14,285 $cm^{-1}$ (corresponds to about 700 to about 1,100 nm). The measured data is evaluated with the aid of a cloud, in which a material database, chemometric models and algorithms are stored, for example.

Further hand-held spectrometers are also obtainable from the company Attonics Systems which operate either in the wave number range from about 9,090 to about 26,315 $cm^{-1}$ (VIS-NIR) or from about 3,333 to about 10,000 $cm^{-1}$ (NIR). These spectrometers are based on interferometers and have a high light throughput and a high spectral resolution (<5 nm for VIS-NIR spectrometer and <20 nm for the NIR spectrometer). The spectrometers have a multi-phase shift array (MPA) chip and an optical arrangement in a circular tube. The spectrometers are also compatible with mobile data processing devices.

Further examples of VIS-NIR spectrometers are the miniature spectrometers "USB2000-VIS-NIR" and "USB4000-VIS-NIR" from the company Ocean Optics. These spectrometers operate with a wavelength range of from about 350 to about 1,000 nm. The spectrometers are connected via a USB connection to a data processing device.

A further suitable, miniaturized NIR spectrometer can be found integrated in the H2 smart phone from the company Changhong.

In addition, there are a series of NIR sensors or NIR evaluation modules that can be used in hand-held spectrometers. Suitable NIR evaluation modules are the "DLP® NIRscan" and "DLP® NIRscan Nano" modules from the company Texas Instruments. These have two tungsten lamps and InGaAs photodiodes as detectors. The module "DLP® NIRscan" operates in a wave number range of from about 4,016 to about 7,407 $cm^{-1}$ and the module "DLP® NIRscan Nano" in the range of from about 5,882 to about 11,111 $cm^{-1}$. The spectroscopic data is communicated wirelessly via Bluetooth Low Energy. With the aid of "Software Developer Kits" (SDK), for example the Open Source SDK from KST Technologies, apps can be developed which evaluate or further process the spectroscopic data.

Further suitable NIR sensors are obtainable under the name "NeoSpectra" from Si-Ware Systems. Specific sensors include: NeoSpectra SW62221-1.7, NeoSpectra SW62221-2.1 and NeoSpectra SW62221-2.5, which operate in different wave number ranges.

It can be preferred if the near-infrared and/or infrared light at least partially comprises a (near-infrared) wave number range of from about 5,022 $cm^{-1}$ to about 4,020 $cm^{-1}$.

In the wave number range of from approximately 6,200 $cm^{-1}$ to approximately 5,500 $cm^{-1}$ cystine demonstrates characteristic absorption bands. If the hair changes, for example due to increasing damage (increase of the cysteic acid content), this can have an effect in the NIR spectrum on the bands at about 5,022 $cm^{-1}$ to about 4,020 $cm^{-1}$ characteristic for cysteic acid.

It is, however, in particular preferred that the near-infrared and/or infrared light at least partially has a (infrared) wave number range of from about 12,820 to about 7,692 $cm^{-1}$ (corresponds to a wavelength range of from 780 to 1,300 nm).

Besides the direct determination of the cysteic acid content via the characteristic absorption bands of cysteic acid, in particular in the range of from about 5,022 $cm^{-1}$ to about 4,020 $cm^{-1}$ (approximately 2,000 to 2,500 nm), an indirect determination of the cysteic acid content can also be performed.

It has surprisingly been found that there is an inverse correlation between the content of cysteic acid and the content of melanin, which makes it possible to determine the content of cysteic acid again indirectly—via the determination of the melanin content. It has been found in particular that the process of oxidative damage (formation of cysteic acid) in the case of bleaching or dyeing of hair is linked to the breakdown of melanin.

The melanin occurring in the hair not only absorbs in the visible spectrum (VIS), but also in the short-wave near-infrared spectrum, i.e. up to approximately 1,300 nm. Without wishing to be tied to this theory, it is supposed that there is additionally a formation of specific oxidation products of melanin, which also have absorptions in the short-wave NIR range.

It has been found that reliable calibration models that produce a correlation between the short-wave near-infrared spectrum and the cysteic acid content and which have substantially the same quality, and also evaluations over the entire or over longer-wave parts of the near-infrared and/or infrared spectral range, in particular longer-wave ranges with characteristic absorptions of the cysteic acid can be created also with the aid of short-wave near-infrared spectra with a wave number range of from about 12,820 to about 7,692 $cm^{-1}$, i.e. in a wave number range in which cysteic acid demonstrates no characteristic absorption.

To summarise, this means that the content of cysteic acid and therefore the determination of a degree of damage of keratin fibers can be determined indirectly via the content of melanin and optionally the oxidation products of melanin in the keratin fibers.

A further advantage with the use of shorter-wave near-infrared radiation, in particular of light in the range of up to about 7,692 $cm^{-1}$ (corresponds to up to about 1,300 nm), preferably in the range of from about 9,090 to about 12,820 $cm^{-1}$ (corresponds to approximately 780 to 1,100 nm) and particularly preferably in the range of from about 9,524 to about 12,500 $cm^{-1}$ (corresponds to approximately 800 to 1,050 nm) for determining hair damage, in particular for determining the cysteic acid content of keratin fibers, is that economical sensors of simple design based on silicon can be used as detectors for recording the NIR light which has interacted with keratin fibres.

At higher wavelength ranges sensors of complex design, which are thus costlier, often have to be used. InGaAs sensors, MCT(HgCdTe) sensors or InSb sensors are thus usually used for the detection of light in a wavelength range of greater than about 1,300 nm.

It has been found that reliable and good calibration models having substantially the same quality, such as evaluations over the entire or over longer-wave parts (>1,300 nm) of the near-infrared and/or infrared spectral range, can be created with sensors based on silicon, In various exemplary embodiments, near-infrared and/or infrared spectra are recorded with the aid of sensors based on silicon.

It has additionally been found that dyeing processes do not interfere with the method for determining an individualized hair treatment, since the chromophores formed during the coloring do not have any absorption in the wavelength range of short-wave near-infrared. This means that the change to the hair colour by the application of dyes does not hinder the ability to determine the damage to the hair and therefore is of no detriment to the suitability of the individualized treatment advice determined depending on the determined degree of damage.

In a preferred embodiment step d) is controlled by a mobile data processing device, in particular a smart terminal. Here, it is preferred if the method is controlled by an app installed beforehand on the smart terminal. Smart terminals comprise smart phones or tablets, in particular.

Within the scope of this application a computer program that is used to process or to assist a non-system-related functionality is referred to as an "app". The term "app" in particular comprises application software for smart terminals such as smart phones and tables ("mobile app") and also desktop application software. The app can be a native app which functions merely on a platform, or a platform-independent web, hybrid or cross platform.

The app may particularly preferably be downloaded via a QR code, an NFC chip, a barcode, or an RFD chip directly at a hairdresser's or at a point of sale (POS) of hair treatment agents.

Alternatively, the app, in particular if it is to be installed on a smart terminal, can be downloaded via an Internet sales platform integrated in the respective operating system of the smart terminal. In the case of a smart terminal with the "Apple iOS" operating system, this sales platform can be the "App Store" for example, or in the case of a smart terminal with the "Android" operating system it can be the "Google Play Store".

In one embodiment the QR code, the NFC chip, the barcode or the RFID chip contains a web link which leads the user of the method to a web page from where the user of the method can download the app.

It is also preferred if the degree of damage determined in the method is output in "% damage" or in a relative indication ("very severe, severe, average, slight, and not at all"). An output in "% damaged" enables a direct comparison of the degrees of damage determined at different times for the same individual. For example, the efficacy of the treatment over time can thus also be monitored.

The degree of damage can be output optically, for example by employing a display device of the (mobile) data processing device, or acoustically, for example by employing a voice message over a loudspeaker.

In a particularly preferred embodiment of the method the individual treatment advice comprises the recommendation of bleaching agents and/or hair colorants and/or haircare products and/or hair styling products.

The recommendation here can include the display or specification of a specific product name of a commercially available bleaching agent and/or hair colourant and/or haircare product and/or hair styling product. Alternatively, the recommendation can include the display or specification of a product line or range, in particular a bleaching agent line/range and/or hair colorant line/range and/or haircare product line/range and/or hair styling product line/range, of a manufacturer.

In an alternative embodiment of the method the individual treatment advice includes a recommendation to abstain for a certain period of time from bleaching and/or oxidative dyeing and/or permanent deformation processes and/or heat treatments. This individual treatment advice can be provided in particular in the event that the determined degree of damage exceeds a certain percentage or in the event that the relative classification of the degree of damage lies in the ranges of "very severe" and/or "severe".

The term "permanent deformation process" includes all processes for curling straight hair or straightening curly hair. These can be permanent waving processes or chemical straightening processes. Besides the use of chemicals, heat treatments can also cause further damage to keratin fibres. Accordingly, the individual treatment advice may include a recommendation to abstain from heat treatments, such as the use of hair curlers or straightening irons, for a certain period of time.

If the keratin fibres for example have a slight to average degree of damage, in a further preferred embodiment of the method the individual treatment advice may include a recommendation to only lighten and/or oxidatively change the hair colour by a maximum number of shades for a certain period of time.

In a further embodiment contemplated herein the individual treatment advice may include a dosing recommendation for a bleaching and/or an oxidative dyeing and/or a prediction of the result of a bleaching and/or oxidative dyeing.

In the case of a bleaching or oxidative dyeing of keratin fibers, the cuticle layer of the keratin fibres is opened in an alkali medium, and a hydrogen peroxide cocktail dosed to a varying degree—depending on the desired bleaching or lightening result—dissolves the natural (color) pigment to a greater or lesser extent. The keratin fiber is made all the lighter, the more highly dosed is the hydrogen peroxide. Bleaching or oxidative dyeing processes always damage keratin fibers noticeably on account of this mode of action. The higher is the concentration of the hydrogen peroxide and the longer is the reaction time, the greater is the damage.

In the case of previously damaged keratin fibres it is therefore advantageous to lighten and/or oxidatively change the hair color only by a maximum number of shades for a certain period of time. In the case of previously damaged keratin fibers it is also advantageous to limit the concentration of the hydrogen peroxide in a dosing recommendation so as to avoid/reduce further (severe) damage caused by the bleaching or dyeing process.

Users increasingly wish to see a realistic impression of how their hair will look after a bleaching or (oxidative) dyeing before the bleaching or (oxidative) dyeing is actually performed. Many providers of bleaching or (oxidative) dyeing processes therefore offer colour consultation apps. For example, hair colors can be tested beforehand in real time with the "Schwarzkopf Frisuren Styleguide" app. To this end, the user downloads the app on a smart terminal and records a photo of their head using the front camera. The software of the app identified the face and head shape. The user then selects a specific bleaching or (oxidative) coloring and the display device of the smart terminal displays how the user will look once this bleaching or (oxidative) dyeing has been performed.

In order to predict the bleaching or dyeing result, the starting hair color is firstly determined, and then the bleaching or dyeing result is calculated on the basis of the specific bleaching or coloring product selected by the user. Since the degree of damage of hair influences the bleaching or dyeing result, the method for determining an individualized hair treatment provides better, in particular more realistic predictions of a result of a bleaching and/or oxidative dyeing. The method for determining an individual hair treatment is preferably part of a color advice app.

In a further, advantageous embodiment of the method, the individual treatment advice lies in encouraging or discouraging the individual to/from using hair treatment products that the user of the method and/or the individual identifies on the basis of QR codes, NFC chips, barcodes or RFID chips.

In this embodiment of the method the user of the method, for example a hairdresser or any person at the point of sale of hair treatment agents, once the degree of damage has been determined by ascertaining the content of at least one hair constituent, can determine suitable or unsuitable hair treatment agents via QR codes, NFC chips, barcodes or RFID chips, which for example are attached to hair treatment agents themselves or to the storage location thereof, for example to the shelf in the hairdresser's or at the point of sale of hair treatment agents.

QR codes, NFC chips, barcodes or RFID chips make it possible to transmit information wirelessly.

An optoelectronically readable marking includes parallel lines and gaps of different widths is understood to be a barcode. The data in a barcode is read automatically by optical readers, such as barcode readers (scanners) or cameras and is further processed electronically. May smart terminals comprise software that makes it possible to detect the code information using the digital camera of the smart terminal and to display this immediately in decoded form to the user.

A QR (quick response) code is a two-dimensional code that includes a square matrix formed of black and white squares which display the coded data in binary form. Smart terminals usually have an installed camera. Once the QR code has been photographed, the QR code is read/interpreted with the aid of software.

NFC chips and RFID chips are transmitter-receiver systems. In this case at least one communication partner must be active, i.e. must prompt the communication. The other partner can be a chip without power supply, for example. This passive part is also referred to as a transponder (=transmitter & responder). Besides the active-passive communication for example between a smart terminal as active communication partner and a transponder/chip, active-active communication is also possible.

The coupling/excitation occurs by magnetic alternating fields in low range generated by the active communication partner or by high-frequency radio waves. Thus, not only is data transmitted, but the transponder is also supplied with energy. The active communication partner, for example a smart terminal, contains a software that controls the actual reading process, and what is known as middleware with interfaces for further (mobile) data processing devices and/or databases.

RFID ("radio-frequency identification") functions via radio waves. RFID technology comprises a very broad offering of various chips and readers which differ in essence by storage capacity, production method, cost, frequency range and by the distance range.

NFC ("near field communication") is a standardised specialisation of RFID technology and was developed specifically for data transmission over short distances (max. 10 cm).

QR codes, NFC chips, barcodes or RFID chips can contain information for example regarding for which degrees of damage the respective hair treatment agent is suitable or unsuitable.

The individual hair treatment advice can also consist for example in determining the chemical composition of a hair treatment agent, in particular a bleaching agent, a hair dye, a haircare product and/or hair styling product.

In an alternative embodiment of the method the individual treatment advice lies in encouraging the individual to use bleaching agents and/or dyes and/or care products that are prepared individually for the individual and in initiating an ordering process, preferably by calling up a web page of a manufacturer of individual bleaching agents and/or individual dyes and/or individual care products.

Customers always wish to obtain a product tailored individually to their own requirements. This can be a product produced especially for the customer or what is known as a "mass customized" product. In the case of a "mass customized" product, however, individualization can be achieved by varying just a few features of a product, although these features are considered to be key features by the customer. These "mass customized" products are preferably based on the concept of modularization, that is to say the product can be composed individually from various modules/building blocks.

There are often numerous dependencies between the multiple different features/ingredients of a product, and these can be expressed as "commands" or "restraints". In order to obtain a clear product definition, it may be advantageous for the ordering process to proceed with the aid of a product configurator. This configurator aids the customer in their selection of the features/ingredients and indicates the reliable/unreliable feature combinations, wherein the latter then are unavailable for selection.

In the case of bleaching agents, dyes, care products and hair styling products for keratin fibers, the relevant product features in particular include the chemical ingredients of the agents, the physical properties of the agents, and the type of formulation of the agents. With the aid of a product configurator, the selection of chemically and/or physically incompatible ingredients or the selection of ingredients unsuitable for the determined degree of damage can be avoided. Conversely, the selection of ingredients suitable for the determined degree of damage can be stipulated or proposed by the product configurator.

It is also preferred that the individual treatment advice is stored and is used during the subsequent course of the process for a long-term recommendation.

In a further embodiment a data comparison is performed between the (mobile) data processing device, in particular the smart terminal, and data that is stored in a cloud, before the treatment advice/recommendation is output to the user. This can be, for example, data from users having the same or similar degrees of damage, gender, age, behaviour patterns, and optionally further identical or similar keratin fiber parameters and the recommendations/measured derived on that basis. By including values obtained from experience, for example in respect of the success of a treatment, the assessment of a suitability of a treatment advice/recommendation can be confirmed or modified for other users. It can thus be made possible for the user to always be provided with an optimal recommendation.

In various exemplary embodiments the individual treatment advice may include the recommendation to seek a hairdresser. In various exemplary embodiments a booking process can be initiated directly via the software/app that determines the individual treatment advice. To this end, the contact data of hairdressers can be stored in the software/app for example and can be displayed to the user. In addition, the selection can be limited via filters, such as post code. In various exemplary embodiments an appointment can be booked directly via the software/app. Alternatively, a hairdressing appointment can be booked via a separate software/app, for example Treatwell.

In a particularly preferred embodiment the wave of the hair is determined in addition to the degree of damage of the keratin fibers, and this is taken into consideration in the individual treatment advice.

In a particularly preferred embodiment the thickness of the hair is determined in addition to the degree of damage of the keratin fibres, and this is taken into consideration in the individual treatment advice.

Besides the degree of damage of the keratin fibers, further properties of the keratin fibers have an influence on the success of a treatment of the keratin fibers. In particular, the wave and/or the thickness of keratin fibers can thus influence the success of a treatment of the keratin fibers. The wave and/or thickness of keratin fibers in particular influences the treatment of keratin fibers with care agents. Since in particular for previously damages keratin fibers a successful treatment with care products is desirable, the consideration of the wave and/or the thickness of the individual treatment advice is particularly advantageous.

The values for the wave and/or thickness of keratin fibers can be determined for example by employing suitable methods by the data processing device, preferably by the smart terminal, on which the method for determining an individualized hair treatment is carried out.

The wave of hair can be determined for example with the aid of image editing and image processing methods. To this end, the user of the method photographs at least part of the hair of the individual. Suitable image editing and image processing programs, such as "ImageJ" determine the linear portion in the image with the aid of suitable plug-ins. Straight hair leads to a high portion of linearity, strongly waved hair leads to a low portion of linearity. The degree of waviness can preferably be specified in "wave %".

The image editing and image processing program for determining the wave can be part of the app for carrying out the method for determining an individualized hair treatment. Alternatively, the determination of the wave with the aid of image editing and image processing methods can be carried out by employing separate methods. The separate method is performed advantageously by an app that is on the mobile data processing device, in particular the smart terminal, which is used to carry out the method for individualized hair treatment. The determined degree of wave can be provided to the method for determining an individualized hair treatment via suitable interfaces.

The wave can be determined via separate methods which are not associated with the method for determining an individualised hair treatment, or can also be determined empirically.

The information regarding wave can be provided via a suitable interface, for example an input window, which opens on the data processing device, preferably the smart terminal, when the method for individualised hair treatment is being carried out. The input window can specify relative degrees of wave, such as "none at all", "hardly any", "light", "medium", "heavy", "very heavy", and the user of the method selects the wave determined subjectively. In the case of a wave percentage determined by a separate method, a specific numerical value, for example 20%, can be input.

The thickness can be determined for example with the aid of an accessory for data processing devices, in particular smart terminals. To this end, a microscope attachment can be clamped over the lens of a smart terminal, for example. Examples of microscope attachments of this kind for smart terminals are the "Nurugo Micro" from the company Nurugo or "μ Peek" from the manufacturer Scrona. The user of the method also determines the thickness of the keratin fibres of the individual before or after the recording of near-infrared and/or infrared spectra of the keratin fibres of the individual (step d). To this end, the user photographs from about 2 to about 20, preferably from about 3 to about 15, and particularly preferably from about 5 to about 10 different keratin fibers together with a size reference with the aid of a microscope attachment. The average hair thickness of the individual is determined using an evaluation software that can be integrated in the app for carrying out the method for individualized hair treatment.

A further alternative method for determining the hair thickness which can be performed with suitable accessory by a data processing device, preferably a smart terminal includes the refraction of laser light.

The hair thickness can be determined via separate methods which are not associated with the method for determining an individualised hair treatment, or can also be determined empirically.

The information regarding hair thickness can be provided via a suitable interface, for example an input window, which opens on the data processing device, preferably the smart terminal when the method for determining an individualized hair treatment is being carried out. The input window can specify relative degrees of hair thickness, such as "thin", "normal" and "thick", and the user of the method selects the hair thickness determined subjectively. In the case of an absolute hair thickness determined by a separate method, a numerical value, for example 80 μm, can be input.

For optimal care, thick hair and (very) heavily waved hair requires hair treatment agents having a high proportion of fat-containing or oil-containing ingredients, whereas haircare products having a low portion of fat-containing or oil-containing ingredients are advantageous for thin and/or straight hair.

In the case of bleaching and oxidative dyeing, the use of hydrogen peroxide in a heavily alkaline medium leads in most cases to (further) damage of the keratin fibres treated in this way. In order to avoid or to reduce damage, agents for bleaching and/or for oxidative dyeing often also themselves contain care substances.

In a particularly preferred embodiment of the method, the individual treatment advice, depending on the determined degree of damage and depending on the thickness and/or the wave, includes a recommendation of bleaching agents and/or hair dyes and/or haircare products and/or hair styling products having a content of fat-containing or oil-containing ingredients adapted to the degree of damage and the thickness and/or wave of the keratin fibres.

Fat-containing and oil-containing ingredients in particular comprise glycerol monoesters, glycerol diesters or glycerol triesters with fatty acids, fatty acids, fatty alcohols, fatty acid mono esters or fatty acid diesters with fatty alcohols, vegetable oils, mineral oils, natural waves and synthetic waxes.

A further important property of the keratin fibres which influences the success of a treatment of the keratin fibers is the degree of greying. The degree of greying of keratin fibers has an effect in particular on the result of a bleaching or oxidative dyeing process.

The degree of greying can be determined via separate methods which are not associated with the method for determining an individualized hair treatment, or can also be determined empirically.

The degree of greying can be determined for example with the aid of image editing and image processing methods. To this end, the user of the method photographs at least part of the keratin fibres of the individual. The photographed part of the keratin fibers preferably includes large parts of the root area. Suitable image editing and image processing programs determine the degree of greying in the image. In a particularly preferred embodiment the determination of the degree of greying is an integral part of the method for individualised hair treatment and is performed by the app that carries out the method for determining an individualized hair treatment.

The information regarding the degree of greying can be provided via a suitable interface, for example an input window, which opens on the smart terminal when the method for individualised hair treatment is being carried out. The input window can specify the degree of greying in a percentage, such as "10%", "30%", "50%", "70%", "90%" and "100%", and the user of the method selects the degree of greying determined subjectively. In the case of a degree of greying percentage determined by a separate method, a numerical value, for example "68%", can be input.

Grey hairs usually take up the oxidation dye precursor products used in oxidative dyeing to a lesser extent than hair that is rich in pigment. This leads to different colouring results depending on the degree of greying of the hair.

In individuals with (very) heavily damaged hair and no or a low degree of greying, the individual treatment advice may therefore consist in discouraging the individual from using bleaching agents and/or dyes and in advising the individual to use colouring processes that do not involve oxidative treatment, for example tinting or intense tinting processes.

In a further aspect the present disclosure relates to a computer program product having a computer-usable medium with computer-readable program codes contained in the medium which, when run, prompt a computer to carry out the steps of the above-described method for determining an individualised hair treatment.

A computer program product, such as a computer program resource, can be provided or delivered for example in form of a storage medium, such as a memory card, a USB stick, a CD-ROM, a DVD, a RAM memory, a ROM memory, a PROM memory, an EPROM memory, a magnetic tape, another storage device suitable for volatile or non-volatile storage of information, or also in the form of a file downloadable from a server in a network. This can be implemented for example in a wireless communication network by the transfer of a corresponding file with the computer program product or the computer program resource.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for determining an individual hair treatment advice, the method comprising:
   a) determining a cysteic acid content of individual keratin fibers from a number of differently damaged keratin fibers by a chromatographic process;
   b) recording a near-infrared and/or infrared spectra of the individual keratin fibers from the number of differently damaged keratin fibers;
   c) creating a calibration model which produces a correlation between near-infrared and/or infrared spectra and the cysteic acid content wherein the calibration model is created as a mathematical model trained using at least one of monitored learning, partially monitored learning, unmonitored learning, corroborated learning and active learning based on the learning data of recorded spectra of the samples of differently damaged keratin fibers;
   d) recording near-infrared and/or infrared spectra of the keratin fibers of an individual;

e) estimating an estimated cysteic acid content of the keratin fibers of the individual on the basis of the calibration model; and f) outputting the individual hair treatment advice regarding the keratin fibers of the individual depending on the estimated cysteic acid content.

2. The method according to claim 1, wherein the calibration model from steps a) to c) is present in the form of stored information on a local data carrier or in a cloud.

3. The method according to claim 1, wherein step d) is performed at a hairdresser's, at a point of sale (POS) of hair treatment agents, or in the private field.

4. The method according to claim 1, wherein step d) is controlled by a smart terminal.

5. The method according to claim 4, wherein step d) is controlled by the smart terminal via a previously installed app.

6. The method according to claim 5, wherein the previously installed app is downloaded via a QR code, an NFC chip, a barcode or an RFID chip directly at a hairdresser's or at a point of sale (POS) of hair treatment agents.

7. The method according to claim 1, wherein the calibration model is a multivariate calibration model.

8. The method according to claim 1, wherein the calibration model takes into account further factors.

9. The method according to claim 8, wherein the further factors comprise categorical factors.

10. The method according to claim 9, wherein the categorical factors comprise ethnicity of the individual, age of the individual and/or hair color of the individual.

11. The method according to claim 1, wherein the individual hair treatment advice comprises a recommendation of bleaching agents and/or hair dyes and/or haircare products and/or styling products.

12. The method according to claim 1, wherein the individual hair treatment advice comprises a recommendation to abstain for a certain period of time from bleaching and/or oxidative dyeing and/or permanent deformation processes and/or heat treatments.

13. The method according to claim 1, wherein the individual hair treatment advice lies in encouraging the individual to use bleaching agents and/or hair dyes and/or haircare products and/or hair styling products that are prepared individually for the.

14. The method according to claim 1, wherein the near-infrared and/or infrared spectra are recorded at least partially in a wave number range of from about 12,820 to about 7692 $cm^{-1}$.

15. The method according to claim 1, wherein a wave of the keratin fibers is determined in response an image processing method of an image captured of the keratin fibers, and is taken into consideration when determining the individual hair treatment advice.

16. The method according to claim 1, wherein a thickness of the keratin fibers is determined in response to an image of the keratin fibers captured using a microscope, and is taken into consideration when determining the individual hair treatment advice.

17. The method according to claim 1, wherein a degree of greying of the keratin fibers is determined in response an image processing method of an image captured of the keratin fibers, and is taken into consideration when determining the individual hair treatment advice.

18. The method according to claim 1, wherein the individual hair treatment advice is output by a display device, or acoustically.

* * * * *